(12) United States Patent
Lloyd et al.

(10) Patent No.: US 8,524,943 B2
(45) Date of Patent: Sep. 3, 2013

(54) PRODUCTION OF TRANS-4-AMINOCYCLOPENT-2-ENE-1-CARBOXYLIC ACID DERIVATIVES

(75) Inventors: Richard Lloyd, Cambridge (GB); Justine Ann Peterson, Royston (GB); Mark Jackson, Cambridge (GB)

(73) Assignees: Dr. Reddy's Laboratories, Inc., Bridgewater, NJ (US); Dr. Reddy's Laboratories Ltd., Hyderabad (IN)

(*) Notice: Subject to any disclaimer, the term of this patent is extended or adjusted under 35 U.S.C. 154(b) by 0 days.

(21) Appl. No.: 13/342,151

(22) Filed: Jan. 2, 2012

(65) Prior Publication Data
US 2012/0101297 A1 Apr. 26, 2012

Related U.S. Application Data

(63) Continuation of application No. PCT/US2010/040897, filed on Jul. 2, 2010.

(60) Provisional application No. 61/222,758, filed on Jul. 2, 2009.

(51) Int. Cl.
*C07B 57/00* (2006.01)

(52) U.S. Cl.
USPC .......................................... 562/115

(58) Field of Classification Search
None
See application file for complete search history.

(56) References Cited

U.S. PATENT DOCUMENTS

| 5,371,282 A | 12/1994 | Nohira et al. |
|---|---|---|
| 6,147,254 A | 11/2000 | Sickles et al. |
| 2004/0167351 A1 | 8/2004 | Bernegger-Egli et al. |

FOREIGN PATENT DOCUMENTS

| WO | 98/10075 A1 | 3/1998 |
|---|---|---|
| WO | 00/58500 A1 | 10/2000 |

OTHER PUBLICATIONS

R. C. Lloyd, et al., "Use of Hydrolases for the Synthesis of Cyclic Amino Acids," Tetrahedron, vol. 60(3), pp. 717-728, 2004.
H. Nakano, et al., "Lipase-Catalyzed Resolution of 2-Azabicyclo[2.2.1]Hept-5-en-3-ones." Tetrahedron: Asymmetry, vol. 7(8), pp. 2381-2386, 1996.

*Primary Examiner* — Yevegeny Valenrod
(74) *Attorney, Agent, or Firm* — Milagros A. Cepeda; Edward D. Pergament; Pergament Gilman & Cepeda LLP

(57) ABSTRACT

Methods of producing compositions of trans-4-amino-2-cyclopentene-1-carboxylic acid derivatives are described. Also described is an amine salt of a compound having formula A,

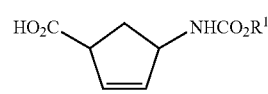

having components present in both cis and trans structures.

23 Claims, No Drawings

PRODUCTION OF TRANS-4-AMINOCYCLOPENT-2-ENE-1-CARBOXYLIC ACID DERIVATIVES

INTRODUCTION

Aspects of the invention relate to methods of producing compositions of trans-4-amino-2-cyclopentene-1-carboxylic acid derivatives.

The trans-4-amino-2-cyclopentene-1-carboxylic acid derivatives represented by structural formula 1, are important intermediates, used in the synthesis of several active pharmaceutical ingredients.

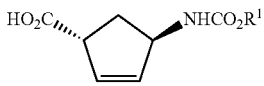

1

International Application Publication No. WO 00/58500 taught a method of making a composition diastereomerically enriched with the trans-4-amino-2-cyclopentene-1-carboxylic acid, 1. As taught in that publication, the first step was epimerization, preferably of the N-protected cis-amino ester, 2,

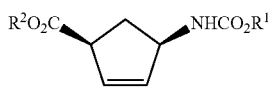

2 to form the complex mixture of reaction products 2, 3, and 4.

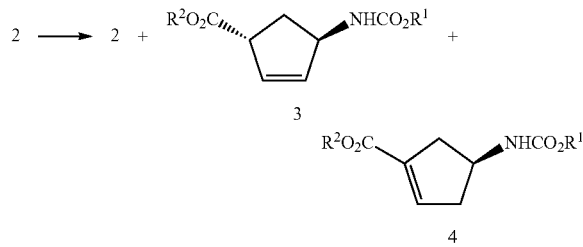

The WO 00/58500 publication teaches that efficient separation of the complex product mixture to isolate substantially pure trans isomer was not possible by crystallization and that chromatographic separation methods were difficult to perform at any appreciable scale. Rather, the publication teaches that separation by selective hydrolysis of the trans-isomer using selective enzymes is possible. See also R. C. Lloyd et al., "Use of hydrolases for the synthesis of cyclic amino acids," *Tetrahedron*, Vol. 60 (3), pp. 717-728, 2004.

Consequently, there is a continuing need for the development of scalable and cost effective process for the preparation of trans-4-amino-2-cyclopentene-1-carboxylic acid derivatives.

SUMMARY

An aspect of the invention provides methods for producing trans-4-amino-2-cyclopentene-1-carboxylic acid derivatives comprising:

(a) providing a composition comprising a compound of formula A,

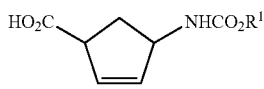

A having components present in both cis- and trans-structures, wherein $R^1$ is an alkyl or aryl group having, in embodiments, up to about 12, or up to about 6 carbon atoms, such as a t-butyl group, in a solvent;

(b) combining the composition with an amine to form salts, wherein the composition is characterized in that some salt precipitates but the salt of the trans structure of compound A remains in the solution in excess of the amount of the salt of the cis structure of compound A remaining in the solution;

(c) separating the precipitate from the solution;

(d) adding acid to the solution to reform carboxylic acids from the salts in the solution;

(e) isolating the compound which is the trans structure of compound A to yield the trans structure of compound A in a diastereomeric excess at least about 80%, or about 85%; and (f) optionally purifying the trans-compound from step (e) to produce a diastereomeric excess of the trans structure of compound A of at least about 98%, by recrystallization.

In an aspect, the present application provides an amine salt of a compound having formula A,

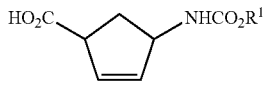

A having components present in both cis and trans structures, where $R^1$ is an alkyl or aryl group having, in embodiments, up to about 12, or up to about 6 carbon atoms, such as a t-butyl group.

DETAILED DESCRIPTION

In an aspect, the invention provides methods for producing trans-4-amino-2-cyclopentene-1-carboxylic acid derivatives comprising:

(a) providing a composition comprising a compound having formula A,

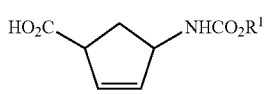

A having components present in both cis- and trans-structures, where $R^1$ is an alkyl or aryl group having, in embodiments, up to about 12, or up to about 6 carbon atoms, such as a t-butyl group, in a solvent;

(b) combining the composition with an amine to form salts, wherein the composition is characterized in that some salt precipitates but the salt of the trans structure of compound A remains in the solution in excess of the amount of the salt of the cis structure of compound A remaining in the solution;

(c) separating the precipitate from the solution;

(d) adding acid to the solution to re-form carboxylic acids from the salts in the solution;

(e) isolating the compound which is the trans-structure of compound A to yield the trans-structure of compound A in a diastereomeric excess at least about 80%, or about 85%; and (f) optionally, purifying the trans-compound from (e) to produce a diastereomeric excess of the trans-structure of compound A of at least about 98%, by recrystallization.

A trans-structure of a compound having formula A may either be the 1R,4R trans species as shown in structure 1,

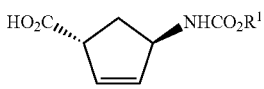
1 or the 1S,4S trans structure.

For convenience, the discussion which follows will be directed to the structure of compound 1, but it should be understood that the 1S,4S trans-species could also be formed instead of the 1R,4R trans-species. The cis-species is shown as compound 5.

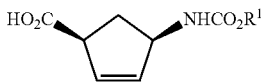
5

A composition comprising compounds 1 and 5 may also comprise other components, such as the conjugated 4-amino-2-cyclopentene-1-carboxylic acid, compound 6.

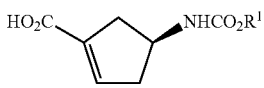
6

Typical solvents for compound A are organic solvents. Examples of useful solvents include, but are not limited to: lower alcohols having up to 6 carbon atoms, or up to 4 carbon atoms, or up to 3 carbon atoms, such as isopropanol, ethanol, and methanol; alkyl acetates, where the alkyl group comprises up to 6 carbon atoms, or up to 4 carbon atoms, such as ethyl acetate and butyl acetate; ethers having up to 10 carbon atoms, such as tert-butyl methyl ether (MTBE); and any mixtures thereof, wherein alkanes such as pentane, hexane or heptane may be present as co-solvents but not as the sole solvents.

A composition comprising compounds 1 and 5 may be formed using any known method. In embodiments, the composition is formed using (1S,4R)-2-aza-bicyclo[2.2.1]heptan-3-one, compound 7, as a starting material. Note that, to form compound 1S,4S trans species, one could begin with (1R,4S)-2-aza-bicyclo[2.2.1]heptan-3-one.

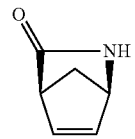
7

This compound may be made using known approaches. See, e.g., International Application Publication No. WO 98/10075, or Hiroto Nakano et al., "Lipase-catalyzed resolution of 2-azabicyclo[2.2.1]hept-5-en-3-ones," *Tetrahedron: Asymmetry*, Vol. 7 (8), pp. 2381-2386, 1996.

According to one approach, compound 7 is esterified in an acidic solution of a lower alcohol as shown in Scheme 1.

Scheme 1

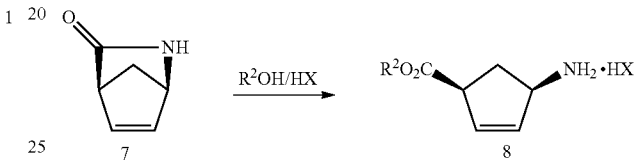

where $R^2$ is any lower alkyl group having up to about four carbon atoms, such as methyl, and HX is any inorganic acid, such as hydrochloric acid.

Suitable alcohols for this transformation include, but are not limited to, methanol, ethanol, 2-propanol, and 1-butanol. The acidic solution can be made by adding thionyl chloride, oxalyl chloride, acetyl, or another acyl chloride, or hydrogen chloride gas to a lower alcohol.

Typically, this addition is done at about 0-10° C., by adding from 0.1 equivalents to 2 equivalents, or about 1.1-1.2 equivalents, of acid, per mole of compound 7. Alternatively, other strong acids, such as sulfuric acid, may be used.

Typically, this reaction is done in 4-5 volumes of the alcohol solvent, although up to 20 volumes can be used. As used herein, "volumes" means the milliliters (mL) of solvent, per gram of reactant.

The nitrogen group is then protected as shown in Scheme 2. This reaction is carried out in about 0-10 volumes, or about 3-5 volumes, of solvent. Typical solvents for the reaction include tetrahydrofuran (THF), dichloromethane, and tert-butyl methyl ether (MTBE).

The base used in this reaction can be any tertiary amine base, such as triethylamine. In a typical procedure, at least one, and up to about 2, or about 1.1-1.3 molar equivalents of base will be used.

Typically, at least 1 equivalent and up to 2 equivalents of the protecting reagent, such as di-tert-butyldicarbonate, are used. The protecting reagent can be, for example, any alkyl or aryl chloroformate, di tert-butyldicarbonate or N-(9H-fluoren-9-ylmethoxycarbonyl)succinimide.

The reaction can be carried out between about 0° C. and 40° C., or about 5-20° C.

Alternatively, this reaction may be carried out in an aqueous system: 8 is dissolved in water (up to 10 volumes, or about 1.5-3 volumes) and the pH is adjusted to about 10-13, or about 11, by adding any metal hydroxide base (e.g., sodium or potassium hydroxide).

The protecting reagent, which is described above (about 1-2 equivalents, or about 1.1 equivalents) is then added in a solvent such as THF (up to 5 volumes, or about 1-3 volumes, or about 2 volumes), while maintaining the pH of the reaction mixture in the range of about 10-13, or about 11, by the addition of the metal hydroxide base.

Scheme 2

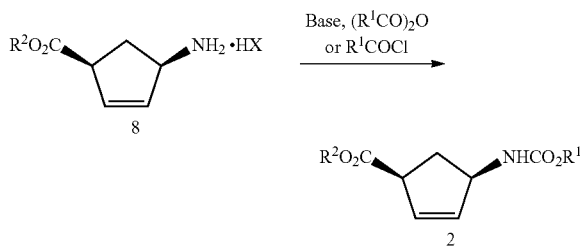

The resulting cis compound 2 is epimerized by any methods, such as is taught, for example, in WO 00/58500, to form alkyl esters of the following formulas 2, 3, and 4:

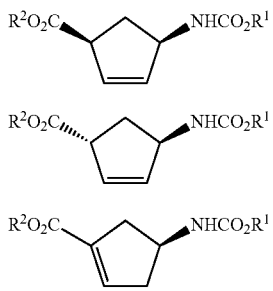

This reaction is carried out in an alcohol solution, such as about 4 volumes, although a range of 1-20 volumes is useful. The choice of alcohol and alcoxide base is restricted by the ester functionality of 2 (for example, for a methyl ester, use sodium methoxide in methanol). Typically, 0.1 molar equivalents, or about 0.05-1 equivalents, of alkoxide base is used. Any metal alkoxide is useful, including sodium and potassium. The reaction temperature is typically about 0° C., or a range of about −10° C. to 10° C. may be used.

In another approach, compound 7 is protected by addition of a protecting group such as any of those mentioned above, including a tert-butoxycarbonyl group, on the nitrogen to give a compound such as 9.

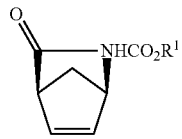

This protection reaction can be carried out as described By S. M. Deluge et al., "An Efficient, Scalable Synthesis of the HIV Reverse Transcriptase Inhibitor Ziagen® (1592U89), *Nucleosides, Nucleotides & Nucleic Acids*, Vol. 19 (1 and 2), pp. 297-327, 2000. Compound 9 may be reacted directly to form the composition comprising the alkyl esters of formulas 2, 3, and 4.

This reaction may be undertaken by treating an alcoholic solution of compound 9 with a catalytic amount of the corresponding alkoxide base. Alcohols include, but are not limited to, methanol, ethanol, 2-propanol, and 1-butanol. Typically, this reaction is carried out in 10-15 volumes of alcohol solvent, although a much wider range of about 2-20 volumes may be used. Up to about 1 molar equivalent of alkoxide may be used, typically in the range of 0.05-0.2 equivalents. Typical temperatures for the reaction are about 0° C., although in practice a range of about −10° C. to 10° C. may be used.

These compounds 2, 3, and 4 then are hydrolyzed to form the compositions comprising compounds 1 and 5. The hydrolysis may be performed by any hydrolysis method. For example, the hydrolysis can be performed using lithium hydroxide, although other metal hydroxides may be used.

In embodiments, the ether solution obtained from the previous reaction is added to the appropriate alcohol (determined by the ester group, using about 2 volumes, although a range of 1 to 5 volumes is useful), prior to the addition of the metal hydroxide as an aqueous solution. The temperature is kept below about 5° C., to minimize formation of compound 6.

The composition comprising compounds 1 and 5 is reacted with an amine to produce an excess of the salt of compound 1 in the solution, relative to compound 5. In embodiments, the salt of compound 5 preferentially precipitates out of the solution.

The salt-forming amine can have the formula $NR^1R^2R^3$, where: $R^1$ is benzyl, or a non-cyclic alkyl or alkenyl group of 3 to 10, or about 3 to 8, carbon atoms; $R^2$ is benzyl, an alkyl group of about 1 to 10, or about 3 to 8, carbon atoms, an alkenyl group of about 3 to 10, or about 3 to 8 carbon atoms, an alkylamino of up to three carbon atoms, or hydrogen; and $R^3$ is benzyl, an alkyl group of about 1 to 10, or about 3 to 8, carbon atoms, an alkenyl of about 3 to 10, or about 3 to 8, carbon atoms, an alkylamino of up to three carbon atoms, or hydrogen; provided that $R^1$ and $R^2$ cannot both be alkyl groups of four or fewer carbon atoms when $R^3$ is hydrogen.

In embodiments, the salt-forming amine is allylamine or 3-dimethylaminopropylamine. The amount of amine added is in a stoichiometric or an excess stoichiometric amount of amine, relative to the total moles of compounds 1 and 5. Generally, about 1 to 1.5 molar equivalents, based on moles of compounds 1 and 5 may be used.

This reaction can be carried out in the solvents described above, including ethyl acetate. The solvent is generally present in 5 to 10 volumes.

After formation of the salts, the precipitate is removed and the carboxylic acids are re-formed by addition of an acid to the solution. The acid added may be hydrochloric acid, although other inorganic acids, such as for example sulfuric, may be used; such that the pH of the final solution is about 2.5.

The compound of formula 1 is then isolated. Isolation may be by crystallization, such as by combination with a lower alkane (less than about 10, or less than about 8, carbon atoms, including at least 5, 6, or 7 carbon atoms, or a heptane). Alternatively, isolation may include solvent removal.

Additional purification and isolation steps may be used, as desired. For example, recrystallization may be used to further increase the diastereomeric purity.

A method of this invention, when the optional step of purification by re-crystallization is used, can achieve compound 1 in a diastereomeric excess greater than about 98%.

In an aspect, the present application provides an amine salt of a compound having formula A,

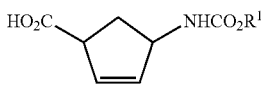

having components present in both cis and trans structures, where $R^1$ is an alkyl or aryl group having, in embodiments, up to about 12, or up to about 6 carbon atoms, such as a t-butyl group.

The salt-forming amine can have the formula $NR^1R^2R^3$, where: $R^1$ is benzyl, or a non-cyclic alkyl or alkenyl group of 3 to 10, or about 3 to 8, carbon atoms; $R^2$ is benzyl, an alkyl group of about 1 to 10, or about 3 to 8, carbon atoms, an alkenyl group of about 3 to 10, or about 3 to 8 carbon atoms, an alkylamino of up to three carbon atoms, or hydrogen; and $R^3$ is benzyl, an alkyl group of about 1 to 10, or about 3 to 8, carbon atoms, an alkenyl of about 3 to 10, or about 3 to 8, carbon atoms, an alkylamino of up to three carbon atoms, or hydrogen; provided that $R^1$ and $R^2$ cannot both be alkyl groups of four or fewer carbon atoms when $R^3$ is hydrogen.

In embodiments, the amine is allylamine or 3-dimethylaminopropylamine.

The following examples will further describe certain specific aspects and embodiments of the invention. These examples are provided only for purposes of illustration, and should not be construed as limiting the scope of the invention in any manner.

EXAMPLE 1

Preparation of (1S,4R)-methyl 4-aminocyclopent-2-enecarboxylate, hydrochloride salt, 10

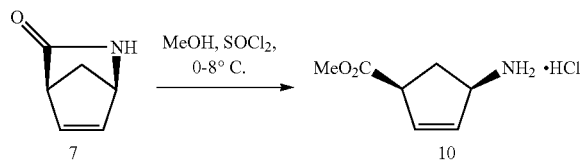 [SMILES: O=C1N[C@H]2C=C[C@@H]1C2 ; COC(=O)[C@@H]1C=C[C@H](N)C1 ; Cl]

Methanol (11 L) is combined with 7 (2.50 kg, 22.91 mol) under nitrogen. The solution is cooled to 0° C. and thionyl chloride (1.88 L, 25.78 mol) is added over 2.5 hours. The mixture is allowed to warm to 8° C., stirred for 16 hours, then concentrated to a volume of 7.5 L. MTBE (20 L) is added and the resulting precipitate is collected and dried to give 10 as an off-white solid (3.74 kg, 92% yield).

$^1$H NMR (400 MHz, MeOH): δ 6.24-6.23 (1H, m), 6.06-6.0.3 (1H, m), 4.40 (1H, brs), 3.81-3.74 (4H, m), 2.77-2.69 (1H, m), 2.22-2.15 (1H, m).

EXAMPLE 2

Preparation of (1S,4R)-methyl 4-(tert-butoxycarbonyl)-aminocyclopent-2-enecarboxylate, 11

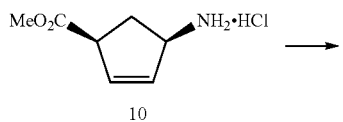

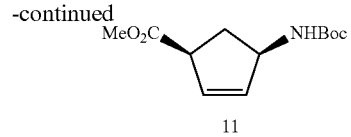

Triethylamine (2.43 L, 17.43 mol) is added to a cooled suspension of 10 (2.55 kg, 14.37 mol) in dichloromethane (10 L), under $N_2$ at 5° C. The mixture is cooled to 0° C., di tert-butyldicarbonate (3.14 kg, 14.40 mol) is added at a rate that maintains the internal temperature of the reaction at 10° C. or less, the addition time being 3.5 hours. The mixture is allowed to warm to room temperature and is then stirred for 16 hours. The mass is washed with water (3 L), 10% $KHSO_4$ solution (3 L), and brine (2×3 L), then the mixture is concentrated. After 9 L of solvent is removed, methanol (2.5 L) is added and the mixture is further concentrated until 2.5 L of solvent is removed, and the mixture is diluted with further methanol (2.5 L) to give the crude product 11 as a methanolic solution.

A sample (2 mL) is removed from the bulk and concentrated to give a neat sample of 11 for analysis.

$^1$H NMR (400 MHz, MeOH): δ 5.91-5.89 (1H, m), 5.82-5.81 (1H, m), 4.64 (1H, brs), 3.57-3.53 (1H, m) 3.37, (3H, s), 3.33-3.33 (1H, m), 2.60-2.52 (1H, m), 1.84-1.78 (1H, m), 1.46 (9H, s).

EXAMPLE 3

Epimerisation of (1S,4R)-methyl 4-(tert-butoxycarbonyl)amino cyclopent-2-enecarboxylate, 11

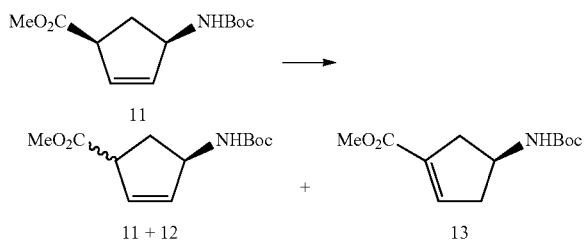

A methanol solution of 11 (10 L, containing about 23.63 mol) is cooled to −2° C. A solution of sodium methoxide (127.6 g, 2.36 mol) in methanol (700 mL) is added over 30 minutes, at a rate that maintains the reaction temperature at 0° C. or less. After 50 minutes, gas chromatography (GC) analysis indicates a product distribution of 43% compound 12, 54% compound 11, and 3% compound 13.

Acetic acid (140 mL) is added over 5 minutes, the mixture is allowed to warm to 10° C., then the mass is concentrated. After 7 L of solvent has been removed, the concentrated mixture is diluted with water (2 L) and MTBE (10 L). The aqueous layer is extracted with further MTBE (1 L). The combined organic layers are concentrated to give the products 11+12+13 in a MTBE solution, with a total volume of 7.5 L.

A sample (2 mL) is removed from the bulk and concentrated further, and this is found to contain 1.5 g of product and therefore 7.5 L should contain 5.625 kg, (99% mass recovery).

GC analysis shows the material to be 44% compound 12, 52% compound 11, and 4% compound 13.

trans Diastereoismer 12; $^1$H NMR (400 MHz, MeOH): δ 5.91-5.87 (1H, m), 5.85-5.81 (1H, m), 4.74 (1H, brs), 3.75-3.72 (1H, m) 3.66, (3H, s), 2.60-2.49 (1H, m), 1.89-1.78 (1H, m), 1.46 (9H, s).

cis Diastereoismer 11; $^1$H NMR (400 MHz, MeOH): δ 5.91-5.87 (1H, m), 5.85-5.81 (1H, m), 4.65 (1H, brs), 3.72, (3H, s), 3.57-3.52 (1H, m), 2.60-2.49 (1H, m), 1.89-1.78 (1H, m), 1.46 (9H, s).

EXAMPLE 4

Ester Hydrolysis

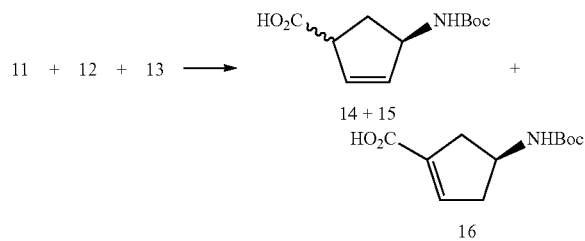

A solution of a mixture of methyl esters 11+12+13 in MTBE (3.5 L, containing about 11.0 mol) is diluted with methanol (4 L) under N$_2$, then cooled to −3.5° C. (jacket temperature −5° C.). A solution of lithium hydroxide monohydrate (508 g, 12.08 mol) in water (2.5 L) is added over 5.5 hours with the reaction temperature being kept below 2° C. at all times during the addition. Once the addition is complete, the mass is stirred for at 2° C. for 30 minutes, then at 10° C. for 16 hours.

The mass is neutralised with 6 M HCl and concentrated. After 4 L of solvent has been removed, the concentrated mixture is acidified to pH 3 by the addition of further 6M HCl. The acidic mixture is extracted with ethyl acetate (10 L, then 2.5 L), and the combined organics are washed with brine (2×1.5 L), then concentrated. Toluene (2×2.5 L) is added during the concentration to aid the removal of water. The products 14+15+16 are recovered as an off white solid (2.67 kg, 94% yield).

trans Diastereoismer 15; $^1$H NMR (400 MHz, MeOH): δ 5.93-5.90 (1H, m), 5.84-5.83 (1H, m), 4.75 (1H, brs), 3.72-3.67 (1H, m), 2.59-2.49 (1H, m), 1.90-1.78 (1H, m), 1.45 (9H, s).

cis Diastereoismer 14; $^1$H NMR (400 MHz, MeOH): δ 5.93-5.90 (1H, m), 5.84-5.83 (1H, m), 4.67 (1H, brs), 3.52-3.48 (1H, m), 2.59-2.49 (1H, m), 1.90-1.78 (1H, m), 1.45 (9H, s).

EXAMPLE 5

Preparation of (1R,4R)-4-(tert-butoxycarbonyl)aminocyclopent-2-enecarboxylic acid, 15

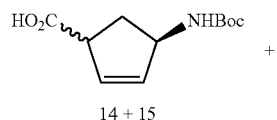

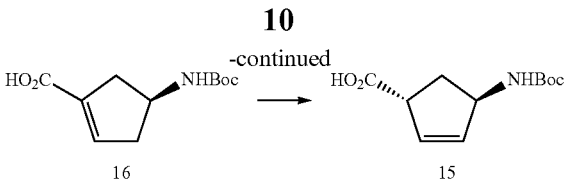

A mixture of 14+15+16 (1.81 kg, 7.99 mol) in ethyl acetate (15 L) is warmed to 50° C. under N$_2$. The resulting cloudy solution is cooled to 8° C. (jacket temperature 5° C.) and 3-dimethylaminopropylamine (1 L, 7.99 mol) is added dropwise over 1.5 hours, keeping the mixture temperature below 15° C. The mixture is stirred at 25° C. for 16 hours. The precipitate is collected and washed with ethyl acetate (2 L).

The combined filtrates are partially concentrated and 8 L of solvent is removed. The concentrated solution is diluted with water (4 L) and acidified to pH 3 by the addition of 6 M HCl, then stirred for 30 minutes. The aqueous layer is washed with ethyl acetate (2.5 L). The combined organic layers are washed with brine (1.5 L) and concentrated to give 15 as an off white solid (550 g, 30% yield).

Liquid chromatography (LC) analysis shows the material to be 88% compound 15, 8% compound 14, and 4% compound 16.

A mixture of 15, 14 and 16 in the ratio described above (1.74 kg, 2.68 mol) is dissolved in MTBE (3.5 L) at 55° C., under N$_2$. The solution is allowed to cool to 40° C. and heptane (7 L) is added. The mixture is cooled to 20° C. and further heptane (1 L) is added to aid stirring. The mass is stirred at 20° C. for 16 hours. The solid material is collected, washed with a 1:3 mixture of MTBE and heptane (2 L) and dried to give 15 as a white solid (1.3 kg, 75% yield).

LC analysis shows the material to be 96.4% compound 15, 2.2% compound 14, and 0.6% compound 16.

This mixture (1.30 kg, 5.73 mol) is dissolved in ethyl acetate (2.6 L) at 60° C., under N$_2$. The solution is allowed to cool to 50° C. and heptane (6 L) is added. The mixture is cooled to 20° C. and stirred for 16 hours. The solid material is collected, washed with a 1:3 mixture of ethyl acetate and heptane (1.5 L) and dried to give 15 as a white solid (1.09 kg, 84% yield).

LC analysis shows the material to be 99.4% compound 15, 0.6% compound 16.

$^1$H NMR (400 MHz, MeOH): δ 5.92-5.90 (1H, m), 5.83-5.82 (1H, m), 4.75 (1H, br), 3.70-3.67 (1H, m), 3.33-3.32 (1H, m), 2.56-2.50 (1H, m), 1.88-1.81 (1H, m), 1.46 (9H, s).

EXAMPLE 6

The procedure of Example 5 is repeated, using the amines and solvents as shown in the table below. The weight ratios of compounds 14:15 in the precipitate and remaining in the solution are shown in the following table.

| Amine | Solvent | Yield (%) | Solid 14:15 | Filtrate 14:15 |
|---|---|---|---|---|
| Benzylamine | i-PrOH | 23 | 8:1 | 1:2.7 |
| Cyclohexylamine | EtOAc | 83 | 1:1.2 | 1:1 |
| Octylamine | EtOAc | 8 | 16:1 | 1:1.6 |
| Isopropylamine | i-PrOH | 16 | 9:1 | 1:2 |
| tert-Butylamine | i-PrOH | 22 | 6:1 | 1:2 |
| tert-Octylamine | i-PrOH | 24 | 5:1 | 1:2 |
| Ethanolamine | No solid | | | |
| Morpholine | EtOAc | 11 | 1:15 | 1.2:1 |
| Methylamine (8M in EtOH) | EtOAc | 53 | 1:1.6 | 1.4:1 |

| Amine | Solvent | Yield (%) | Solid 14:15 | Filtrate 14:15 |
|---|---|---|---|---|
| Dibenzylamine | EtOAc | 22 | 1.5:1 | 1:2 |
| (S)-(−)-α-Methylbenzylamine | i-PrOH | 35 | 1:1.4 | |
| (R)-(+)-α-Methylbenzylamine | i-PrOH | 56 | 1:1 | |
| Pyrrolidine | No solid | | | |
| Piperidine | No solid | | | |
| Allylamine | i-PrOH | 28 | 7:1 | 1:2.8 |
| Allylamine | EtOAc | 49 | 6.8:1 | 1:12 |
| 3-Dimethylaminopropylamine | EtOAc | 37 | 16:1 | 1:6 |
| Dicyclohexylamine | i-PrOH | 45 | 1:2.4 | 1.8:1 |
| Dibutylamine | No solid | | | |

EXAMPLE 7

Opening (1R,4S)-tert-butyl 3-oxo-2-aza-bicyclo[2.2.1]hept-5-ene-2-carboxylate to give epimer mixture 11+12+13

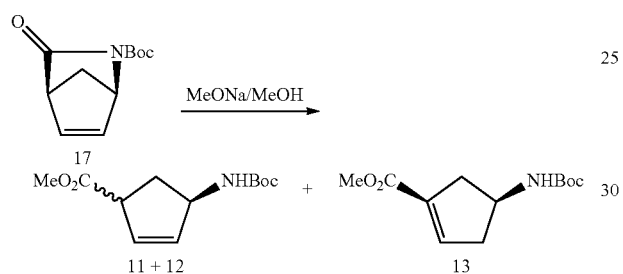

Compound 17 (7.5 g, 35.89 mmol) is dissolved in methanol (100 mL) at 1.5° C. A solution of sodium methoxide (0.19 g, 3.59 mmol) in methanol (5 mL) is added over 10 minutes, with the mixture temperature being kept below 2° C. during the addition. After 100 minutes, GC analysis indicates a product distribution of 36% compound 12, 62% compound 11, 2% compound 13.

The reaction is quenched by the addition of acetic acid (0.2 mL) and the mixture is concentrated to remove methanol. The residue is partitioned between water (30 mL) and MTBE (80 mL) and the aqueous layer is extracted with MTBE (40 mL). The combined organic layers are dried over sodium sulfate and concentrated to give methyl esters 11+12+13 as a pale yellow oil (8.45 g, 104% yield).

GC analysis indicates a product distribution of 37% compound 12, 62% compound 11, and 1% compound 13.

EXAMPLE 8

Opening (1S,4R)-tert-butyl 3-oxo-2-aza-bicyclo[2.2.1]hept-5-ene-2-carboxylate 18 to give epimer mixture 19+20+21

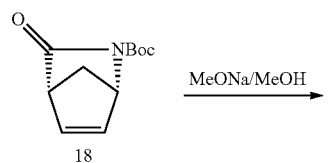

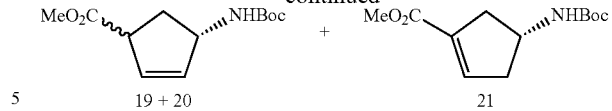

Compound 18 (75.3 g, 360 mmol) is dissolved in methanol (1.2 L) at 1.5° C. A solution of sodium methoxide (3.9 g, 72.1 mmol) in methanol (50 mL) is added over 10 minutes, and the mixture temperature is kept below 2° C. during the addition. After 300 minutes, GC analysis indicates a product distribution of 43% compound 19 (trans diastereoisomer), 55% compound 20 (cis diastereoisomer), and 2% compound 21.

The pH is adjusted to 6 with acetic acid, added over 5 minutes, and the mixture is allowed to warm to 10° C., then concentrated. After 1.2 L of solvent has been removed, the concentrated mixture is diluted with water (200 mL) and MTBE (750 mL). The aqueous layer is extracted with further MTBE (250 mL). The combined organic layers are concentrated to give methyl esters 19+20+21 (87 g).

GC analysis shows the material to be 44% compound 19 (trans diastereoisomer) 54% compound 20 (cis diastereoisomer) and 2% compound 21.

$^1$H NMR: data as above for compounds 11 (cis diastereoisomer) and 12 (trans diastereoisomer).

EXAMPLE 9

Ester Hydrolysis

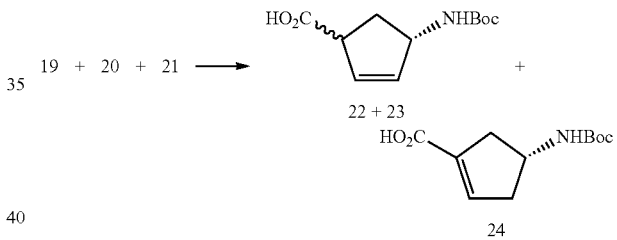

A mixture of methyl esters 19+20+21 (87 g) is dissolved methanol (800 mL) under $N_2$, then cooled to −3.5° C. (jacket temperature −5° C.). A solution of lithium hydroxide monohydrate (18.2 g, 432 mmol) in water (150 mL) is added over 30 minutes, with the mixture temperature being kept below 0° C. at all times during the addition. After the addition is complete, the mixture is stirred at 2° C. for 16 hours.

A sample (2 mL) is removed from the mass, quenched with acetic acid, and extracted into MTBE (5 mL). Solvent is removed to give a neat sample for analysis. NMR analysis shows the material to be 43% 19+20+21.

Additional LiOH (2.0 g, 47.5 mmol) is added and the mixture is stirred at 0° C. for 4 hours. NMR analysis shows the material to be 30% 19+20+21.

Additional LiOH (9.0 g, 213 mmol) is added and the mixture is stirred at 0° C. for 72 hours. The mass is cooled to −2° C. before being neutralized with 6 M HCl and concentrated. After 1.2 L of solvent has been removed, the concentrated mixture is acidified to pH 5 by the addition of further 6M HCl. The acidic mixture is extracted with ethyl acetate (800 mL, then 400 mL), and the combined organic layers are washed with brine (400 mL, then 200 ml), then concentrated. The products 22+23+24 are recovered as an off-white solid (83 g).

$^1$H NMR: data as above for compounds 14 (cis diastereoisomer) and 15 (trans diastereoisomer).

EXAMPLE 10

Preparation of (1S,4S)-4-(tert-butoxycarbonyl)aminocyclopent-2-enecarboxylic acid, 22

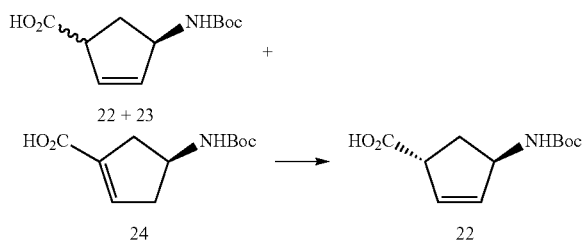

The mixture of 22+23+24 (83 g, 385 mmol) in ethyl acetate (600 mL) is warmed to 50° C. under $N_2$. The resulting cloudy solution is cooled to −2° C. and 3-dimethylaminopropylamine (52.5 mL, 0.417 mol) is added drop-wise over 30 minutes, keeping the temperature below 2° C. The mixture is stirred at 25° C. for 16 hours. The precipitate is collected and washed with ethyl acetate (75 mL).

The combined filtrates are diluted with water (600 mL) and acidified to pH 2.5 by the addition of 6 M HCl, then stirred for 30 minutes. The aqueous layer is washed with ethyl acetate (100 mL). The combined organic layers are washed with brine (2×300 mL) and concentrated to give 22 as an off-white solid (26 g, 31% yield). LC analysis shows the material to be 92% compound 22, 5% compound 23, and 1% compound 24.

A mixture of 22, 23 and 24 in the ratio described above (26 g, 114 mmol) is dissolved in ethyl acetate (52 mL) at 60° C., under $N_2$. The solution is allowed to cool to 50° C. and heptane (120 mL) is added. The mass is cooled to 20° C. and stirred for 16 hours. The solid material is collected, washed with a 1:3 mixture of ethyl acetate and heptane (1.5 L) and dried to give 22 as a white solid (15 g, 58% yield).

LC analysis shows the material to be 99.8% compound 22, 0.2% compound 24.

$^1$H NMR: data as above for compound 15.

The invention claimed is:

1. A process for preparing trans-4-amino-2-cyclopentene-1-carboxylic acid derivatives represented by formula 1, comprising:

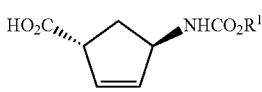

1 a) providing a composition comprising a compound of formula A,

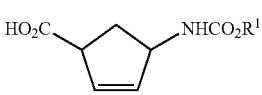

A having components present in both cis- and trans-structures, wherein $R^1$ is an alkyl or aryl group having up to 12 carbon atoms, in a solvent;
b) combining with an amine to form salts, wherein some salt precipitates but the salt of a trans-structure of compound A remains in the solution in excess of the amount of the salt of the cis-structure of compound A remaining in the solution;
c) separating the precipitate from the solution;
d) adding acid to the solution to re-form carboxylic acids from the salts in the solution;
e) isolating the compound 1, which is the trans-structure of compound A; and
f) optionally, purifying the composition from e) to produce a diastereomeric excess of the trans-structure of compound A.

2. The process of claim 1, wherein a composition comprising
compounds of formula A is obtained by hydrolyzing a mixture including compounds 2, 3 and 4,

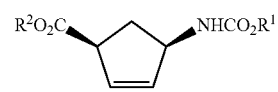

2

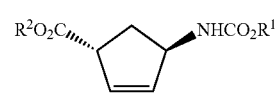

3

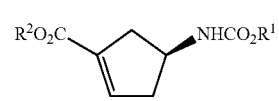

4 where $R^1$ is an alkyl or aryl group having up to 12 carbon atoms, and $R^2$ is a lower alkyl group having up to about four carbon atoms.

3. The process of claim 1, wherein a solvent in a) is a lower alcohol, alkyl acetate, ether, or a mixture of two or more thereof.

4. The process of claim 3, wherein an alkyl acetate is ethyl acetate.

5. The process of claim 1, wherein a salt-forming amine has the formula $NR^1R^2R^3$, where: $R^1$ is benzyl, or a non-cyclic alkyl or alkenyl group of 3 to 10 carbon atoms; $R^2$ is benzyl, an alkyl group of about 1 to 10 carbon atoms, an alkenyl group of about 3 to 10 carbon atoms, an alkylamino of up to three carbon atoms, or hydrogen; and $R^3$ is benzyl, an alkyl group of about 1 to 10 carbon atoms, an alkenyl of about 3 to 10 carbon atoms, an alkylamino of up to three carbon atoms, or hydrogen; provided that $R^1$ and $R^2$ cannot both be alkyl groups of four or fewer carbon atoms when $R^3$ is hydrogen.

6. The process of claim 1, wherein a salt-forming amine is allylamine or 3-dimethylaminopropylamine.

7. The process of claim 1, wherein about 1 to 1.5 moles of amine is used, per mole of compound of Formula A.

8. The process of claim 1, wherein the acid used in d) is an inorganic acid.

9. The process of claim 1, wherein the acid used in d) is hydrochloric acid or sulfuric acid.

10. The process of claim 1, wherein the solution has an excess of the salt of compound 1, relative to compound 5,

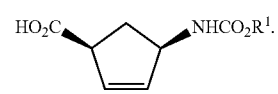

5

11. The process of claim 1, wherein the compound of formula 1 is isolated by crystallization, after combining a solution containing the compound of formula 1 with a lower alkane.

12. The process of claim 11, whereon wherein a lower alkane has less than 10 carbon atoms.

13. The process of claim 1, wherein the compound of formula 1 is isolated by solvent removal.

14. The process of claim 1, further comprising recrystallizing the compound of formula 1 from a suitable solvent.

15. The process of claim 1, wherein the compound of formula 1 is in a diastereomeric excess greater than about 98%.

16. A compound which is an amine salt of a compound having formula A,

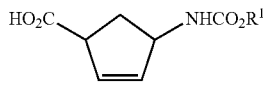

A having components present in both cis and trans structures, wherein $R^1$ is an alkyl or aryl group having up to 12 carbon atoms and wherein the salt-forming amine has the formula $NR^1R^2R^3$, where: $R^1$ is benzyl, or a non-cyclic alkyl or alkenyl group of 3 to 10 carbon atoms; $R^2$ is benzyl, an alkyl group of about 1 to 10 carbon atoms, an alkenyl group of about 3 to 10 carbon atoms, an alkylamino of up to three carbon atoms, or hydrogen; and $R^3$ is benzyl, an alkyl group of about 1 to 10 carbon atoms, an alkenyl of about 3 to 10 carbon atoms, an alkylamino of up to three carbon atoms, or hydrogen; provided that $R^1$ and $R^2$ cannot both be alkyl groups of four or fewer carbon atoms when $R^3$ is hydrogen.

17. The compound of claim 16, wherein $R^1$ is an alkyl or aryl group having up to 6 carbon atoms.

18. The compound of claim 16, wherein $R^1$ is a t-butyl group.

19. The compound of claim 16, wherein a salt-forming amine is allylamine or 3-dimethylaminopropylamine.

20. The process of claim 4, wherein a mixture including compounds 2, 3 and 4 is prepared by a process comprising reacting an alcohol solution of compound 9 with a catalytic amount of an alkoxide base;

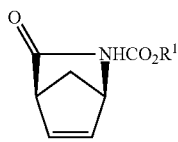

9 wherein,
$R^1$ is an alkyl or aryl group having up to about 12 carbon atoms.

21. The process of claim 19, where an alcohol is methanol, ethanol, 2-propanol, or 1-butanol.

22. The process of claim 19, wherein the reaction is carried out in 2-20 mL of alcohol solvent, per gram of compound 9.

23. The process of claim 19, wherein less than about 1 molar equivalent of alkoxide is used, per mole of compound 9.

* * * * *